(12) United States Patent  (10) Patent No.: US 7,730,790 B2
Sykes  (45) Date of Patent: Jun. 8, 2010

(54) SHEAR TEST DEVICE (75) Inventor: Robert John Sykes, Essex (GB)

(73) Assignee: Nordson Corporation, Westlake, OH (US)

( * ) Notice: Subject to any disclaimer, the term of this patent is extended or adjusted under 35 U.S.C. 154(b) by 110 days.

(21) Appl. No.: 11/573,005

(22) PCT Filed: Aug. 5, 2005

(86) PCT No.: PCT/GB2005/003105

§ 371 (c)(1),
(2), (4) Date: Sep. 11, 2008

(87) PCT Pub. No.: WO2006/016136

PCT Pub. Date: Feb. 16, 2006

(65) Prior Publication Data

US 2008/0314159 A1    Dec. 25, 2008

(30) Foreign Application Priority Data

Aug. 10, 2004 (GB) ................................. 0417773.9
Jul. 6, 2005 (GB) ................................. 0513896.1

(51) Int. Cl.
G01N 3/24 (2006.01)
(52) U.S. Cl. .......................................... 73/842; 73/760
(58) Field of Classification Search ............ 73/760–842
See application file for complete search history.

(56) References Cited

U.S. PATENT DOCUMENTS

| 3,603,152 | A | * | 9/1971 | Alibert et al. | ................. 73/723 |
| 3,662,312 | A | | 5/1972 | Thorp et al. | |
| 3,756,289 | A | * | 9/1973 | Rotert et al. | .................... 140/2 |
| 3,805,601 | A | | 4/1974 | Jeffers | |
| 3,821,785 | A | | 6/1974 | Rose | |
| 4,280,350 | A | * | 7/1981 | King et al. | ..................... 72/8.8 |
| 4,869,043 | A | * | 9/1989 | Hatzinikolas et al. | ......... 52/712 |
| 5,564,170 | A | * | 10/1996 | Flemmer et al. | ............... 29/20 |
| 5,958,270 | A | * | 9/1999 | Cho | .......................... 219/221 |
| 6,041,996 | A | * | 3/2000 | Arikado | ................. 228/180.22 |
| 6,131,795 | A | * | 10/2000 | Sato | ............................ 228/102 |
| 6,341,530 | B1 | * | 1/2002 | Sykes | .......................... 73/831 |
| 6,901,795 | B2 | * | 6/2005 | Naguib et al. | ............. 73/204.27 |
| 7,413,108 | B2 | * | 8/2008 | Vasquez et al. | .......... 228/180.5 |
| 7,500,378 | B2 | * | 3/2009 | Tsai et al. | .................. 73/12.09 |

(Continued)

FOREIGN PATENT DOCUMENTS

EP    0772036 A2    5/1997

(Continued)

OTHER PUBLICATIONS

European Patent Office, International Search Report and Written Opinion in Serial No. PCT/GB2007/000528, May 9, 2007.

Primary Examiner—Max Noori
(74) Attorney, Agent, or Firm—Wood, Herron & Evans, LLP (57) ABSTRACT Shear test apparatus for gold and solder balls of a semiconductor substrate comprises a support element (21) on which is provided a piezo electric crystal (24) in the direct shear load path. The crystal (24) may have a shield (25). The interface between shield and crystal, and crystal and support element may include an epoxy resin layer to distribute force and retain the components as a unit.

22 Claims, 5 Drawing Sheets

U.S. PATENT DOCUMENTS 7,555,961 B2 * 7/2009 Sykes .................... 73/841
2006/0011703 A1 * 1/2006 Arita et al. ................ 228/56.3

FOREIGN PATENT DOCUMENTS

| GB | 1094862 A | 12/1967 |
| GB | 2174241 A | 10/1986 |
| JP | 1174935 A | 7/1989 |
| SU | 1727039 A1 | 4/1992 |
| WO | 00/75624 A1 | 12/2000 |
| WO | 2004083831 A1 | 9/2004 |
| WO | 2005/114722 A1 | 12/2005 |
| WO | 2007/093799 A2 | 8/2007 |

* cited by examiner fig 3 fig 4 fig 5

SHEAR TEST DEVICE

This invention concerns a device for testing the shear strength of a bond in a semi-conductor device, and more particularly the strength of a bond between a substrate and a means of electrical connection thereto, typically a part-spherical deposit of solder or gold.

Semiconductor devices are very small, typically from 0.2 mm square to 25 mm square. These devices have sites for the bonding of electrical conductors thereto. Sites typically comprise part spherical deposits of gold or solder, collectively known as balls, which in use have the appearance of a squashed sphere or low circular dome, and a diameter in the range 50-1000 µm. These deposits form part of the electrical path between, for example, a printed circuit board and a chip, and may directly connect components, or may be joined to a conductor which is itself connected to another component. Many such balls may be provided as a regular grid-like array on a substrate.

Discrete balls are typically applied to a substrate and reflowed during subsequent connection to another component.

It is necessary to test the mechanical strength of the bond between the gold or solder deposit and the substrate in order to give confidence that the bonding method is adequate, and that the bond strength is sufficient. Difficulties arise because of the very small dimensions of the components, the precision with which the testing device must be positioned, and the very small forces and deflections which are to be measured.

It has been proposed to test the shear strength of such deposits by applying a tool to one side thereof. In order to avoid friction caused by the tool rubbing on the surface of the substrate, it is necessary for the tool to be just above the substrate surface. The height of the tool above the substrate must be closely controlled, typically within ±0.001 mm, to give accurate force measurement.

A known shear test apparatus comprises a machine having a support surface and a test head movable in a controlled manner relative to the support surface. The test head carries a cartridge specific to the test to be performed and having one of several interchangeable tools thereon. Typically the tool will be sized and/or shaped to suit the ball deposit to be tested. In use the substrate to be tested is attached to the support surface, and the tool is driven relatively against the ball deposit to perform the required test, which may be for example a shear test or a reciprocating fatigue test.

It will be understood that a typical tool is very small, and accordingly the cartridge has a flexible element on which is mounted one or more force gauges (such as strain gauges). Thus shear force between the tool and ball deposit is measured at a distance by deflection in the cartridge.

In the case of impact testing, where the tool is moving at high velocity before contact with the ball deposit, shear forces are not easy to detect. This is because the strain gauged element is somewhat remote from the tool, and the inertia of the cartridge masks the forces being measured. Typically the speed of the test is sufficiently high that the test is over before the strain gauge has time to respond to the forces at the tool.

According to a first aspect of the invention there is provided a test apparatus for applying shear loads to a ball deposit of gold or solder on a substrate, the apparatus comprising a support element, and a piezoelectric crystal on the support element, the support element being adapted to apply a shear load to a ball deposit via said crystal, thus placing the crystal under stress and causing an electrical signal to emanate therefrom.

Preferably the apparatus further includes a shield for the crystal, so that shear load is applied to the ball deposit via the shield.

The shield may comprise a protective surface applied directly to the crystal, or may be a tool element mounted on the support element and adapted to bear against the crystal.

Such a tool element may be arranged to pre-load the crystal so as to improve stability thereof.

The shield may be adapted to the shape of the ball deposit to be tested, for example by having a part spherical recess adapted to engage a portion of the circumference of the ball deposit.

In a preferred embodiment the interface between the support element and the crystal, and/or between the crystal and the shield comprises a force distributing layer which is adapted to give substantially uniform planar contact. Such a layer may for example comprise an epoxy resin which is spread whilst fluid onto the respective interface surfaces, and cures after assembly of the apparatus to ensure that planar contact occurs. In this way point and line loads can be avoided.

The layer need only be very thin, and sufficient only to accommodate any misalignment which may be present. A particular advantage of epoxy resin is that the adjacent components are also retained in one another adhesively, so that the apparatus becomes unitary.

The layer may also provide an electrical insulator for the crystal or, depending on the electrical pathways, may be electrically conductive.

According to a second aspect of the invention there is provided a device for calibrating an apparatus adapted to apply shear loads to a ball deposit of gold or solder on a substrate, the device comprising a plate element having a flat surface and a through aperture at right angles to said surface, said aperture being sized to receive a wire of gold or solder whereby the wire is indexed to protrude above said surface, and said device is adapted to apply a shear load thereto.

A wire of gold or solder can very closely relate to the respective ball deposit, and hence give accurate calibration of one shear tool apparatus with respect to another. The device may include means for indexing a wire through said aperture on demand, and for determining the protrusion of wire above said surface per indexation. The means for indexing may be motor driven.

According to the second aspect, there is also provided a method of calibrating a shear tool for ball deposits of gold or solder, the method comprising the steps of:

providing a flat surface with a through aperture at right angles thereto, providing a wire of gold or solder in said aperture, indexing said wire to protrude above said surface, and conducting a shear test with said tool against the protruding portion of said wire.

Wire is a consistent material, and well suited to repeat testing since the shear forces detected are closely repeatable. Accordingly successive shear tests using different shear tools can be correlated, and the shear sensors of the respective tools can be calibrated against a consistent standard.

The mechanical properties of wires are usually well known, and accordingly the shear forces detected using the method can be related to absolute as well as relative values.

Other features of the invention will be apparent from the following description of several preferred embodiments shown by way of example in the accompanying drawings, in which.

Figures 1, 2:
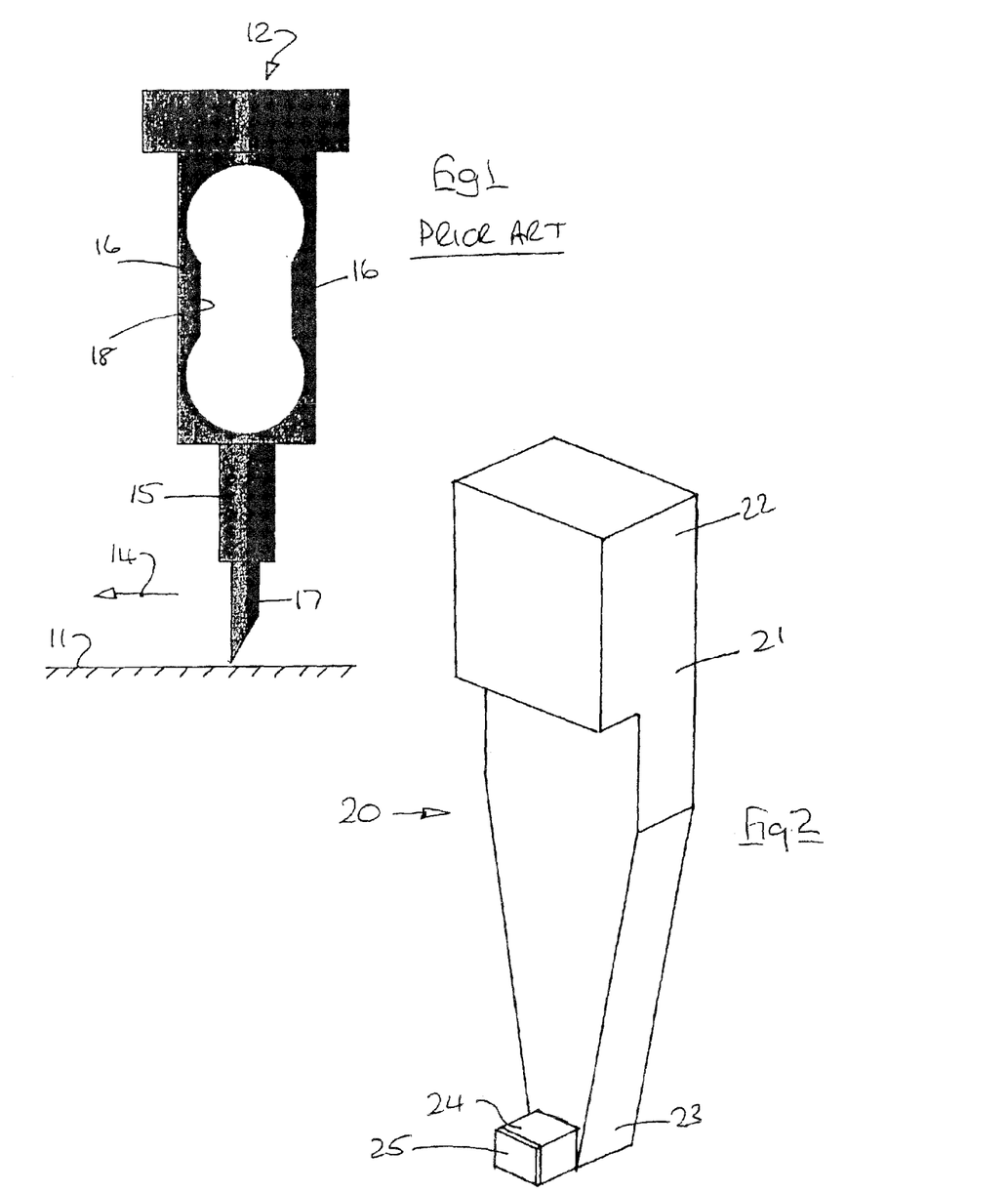
FIG. 1 schematically illustrates a prior test device.
FIG. 2 schematically illustrates on an enlarged scale, a test device according to the invention.

With reference to the drawings FIG. 1 shows a prior test apparatus comprising a support surface 11, and a test head 12 movable relative thereto horizontally (XY) and vertically (Z). The test head comprises a cartridge to which a tool mounting 15 is attached by parallel arms 16. A test tool 17 is provided on the tool mounting 15.

In use the tool is moved sideways in the direction of arrow 14 against a ball deposit mounted on the surface 11 to conduct a shear test, and the force is determined by strain gauges responsive to deflection of the arms 16. The tip of the test tool 17 is typically very small, and of the order of the diameter of the ball deposit, i.e. in the range 50-1000 μm.

FIG. 2 shows a first embodiment of the invention, and illustrates a tool 20 comprising a support element 21, the upper end 22 of which is adapted for direct connection to a prior art test head 12, or to a cartridge thereof in any suitable manner. The latter arrangement ensures interchangeability of components for existing test apparatus.

The lower end 23 tapers and has a piezo-electric crystal 24 attached thereto. The outer face of the crystal has a shield 25. The crystal is illustrated as a cube, but other shapes are of course possible, such as a cylinder.

The crystal has a width generally of the same order as the ball deposit to be tested, for example 100 μm. Not illustrated are the usual electrical connections of the crystal whereby changing stress of the crystal can be detected, and by calibration, calculation of the actual load.

The shield can be any suitable material covering adapted to protect the crystal from mechanical damage yet allow loads to be fully transmitted thereto. For example the shield may comprise a thin metal plate bonded to the crystal.

Figure 3:
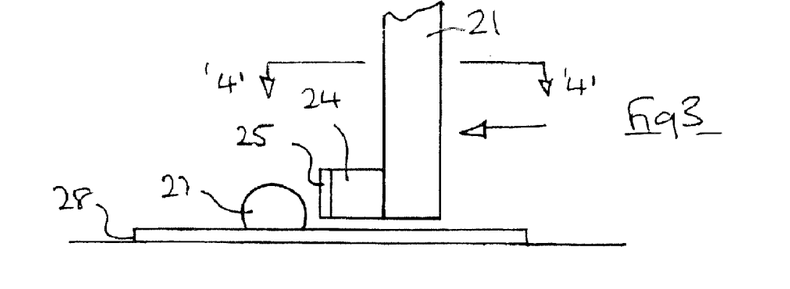
FIG. 3 illustrates a typical shear test in side elevation.

FIG. 3 illustrates the device of FIG. 2 in use and about to apply a shear load in the direction of arrow 26 against a ball deposit 27 mounted on a substrate 28.

Figure 4:
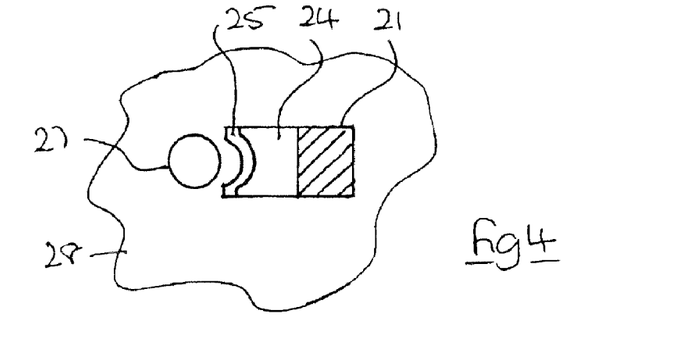
FIG. 4 is a view on line 4-4 of FIG. 3.

The sectional view of FIG. 4 shows how the shield and crystal may be adapted to the curved shape of the ball deposit 27.

Figure 5:
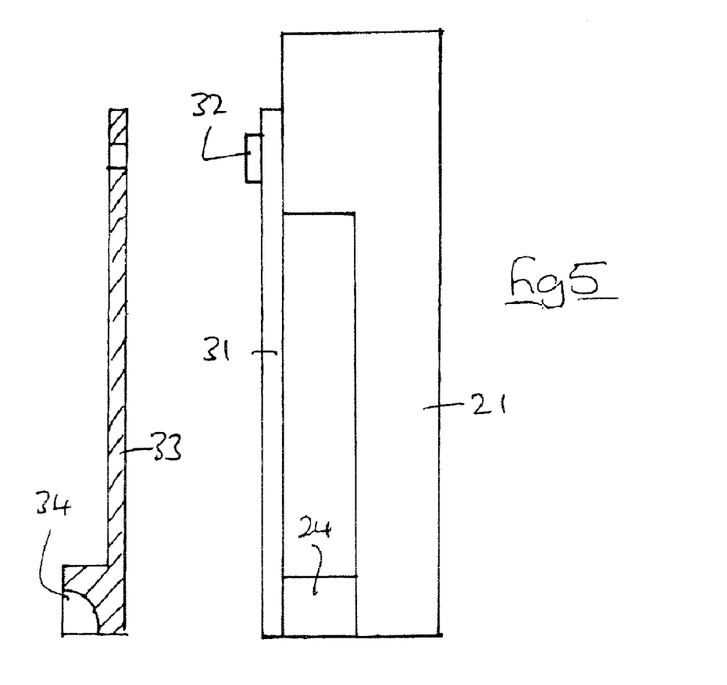
FIG. 5 is an alternative tool in side elevation, with a tool element shovel in longitudinal section.

A second embodiment is illustrated in FIG. 5 and comprises the support element 21 from which an anvil 31 is suspended on a pin 32 or clip of any suitable kind. The tool is plate-like and can directly apply a compressive load to the crystal 24. In a preferred embodiment the tool is biased against the crystal by internal resilience thereof, for example by reducing the thickness of the portion in contact with the upper end 22.

An alternative anvil 33 is illustrated in section, and has a part spherical recess 34 to closely engage the ball deposit.

Figure 6:
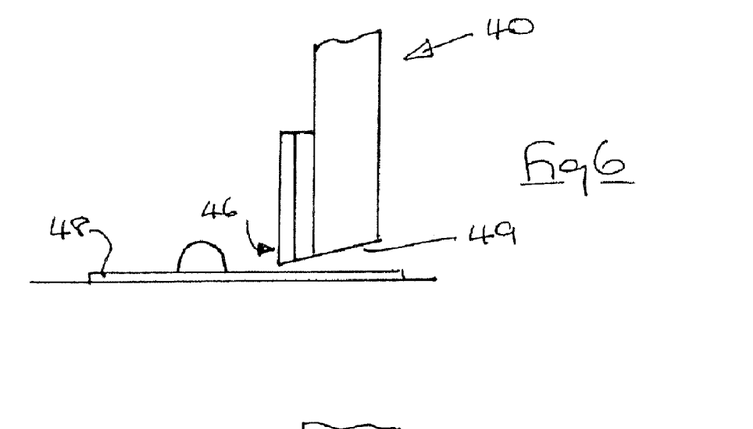
FIGS. 6-8 show alternative tools inside elevation.

FIG. 6 illustrates an alternative embodiment in which the undersurface of a tool 40 has an upward rake 49 so that the height of the leading edge 46 above the substrate 48 can be accurately determined prior to shear test. The rake may be any suitable angle (typically in the range 15-30°) which ensures clearance behind the leading edge whilst maintaining mechanical integrity of the tool.

Figure 7:
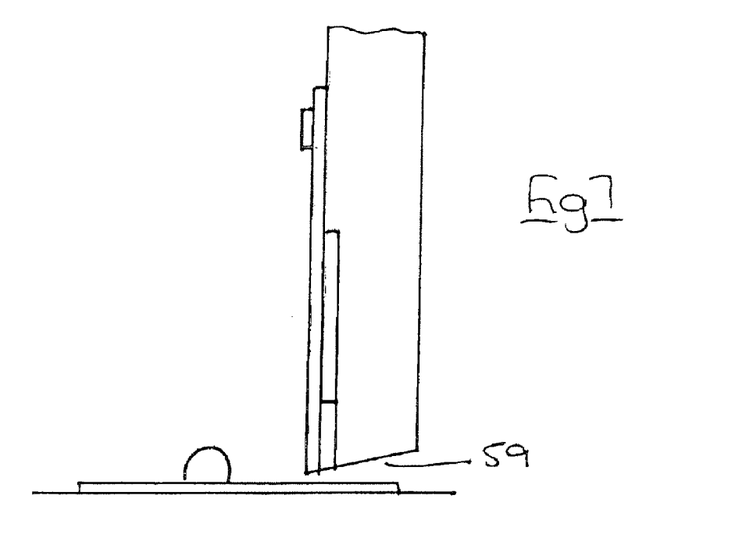
Figure 8:
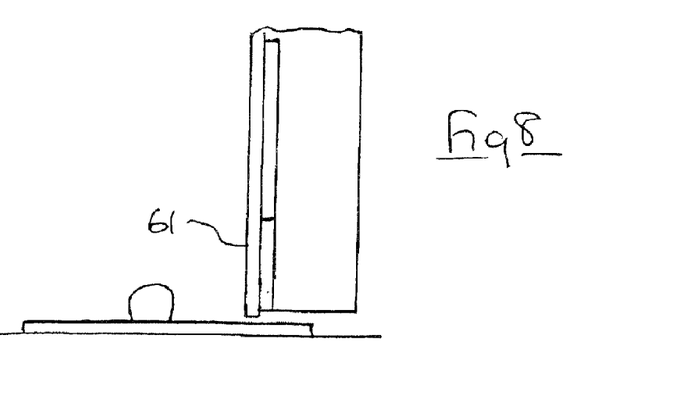

FIG. 7 corresponds to FIG. 5, and shows a similar negative rake 59. FIG. 8 shows an alternative anvil 61 which projects downwardly, as illustrated, so that a negative rake to the remainder of the tool is not required.

Figure 9:
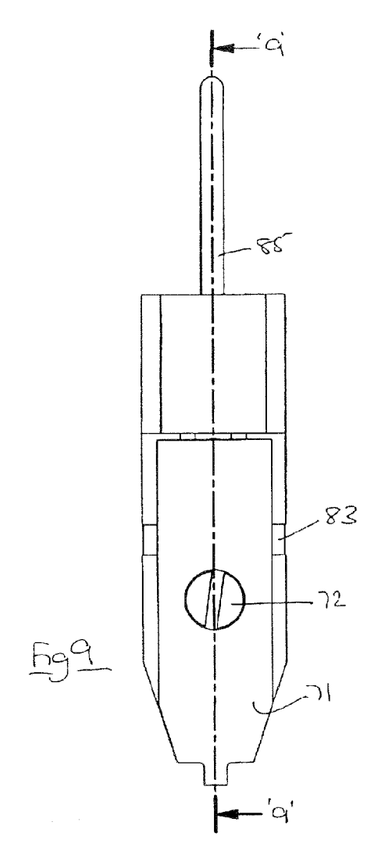
FIG. 9 shows a tool in front elevation.

FIGS. 8 and 9 show an example arrangement of component parts of a typical tool 70.

Figure 10:
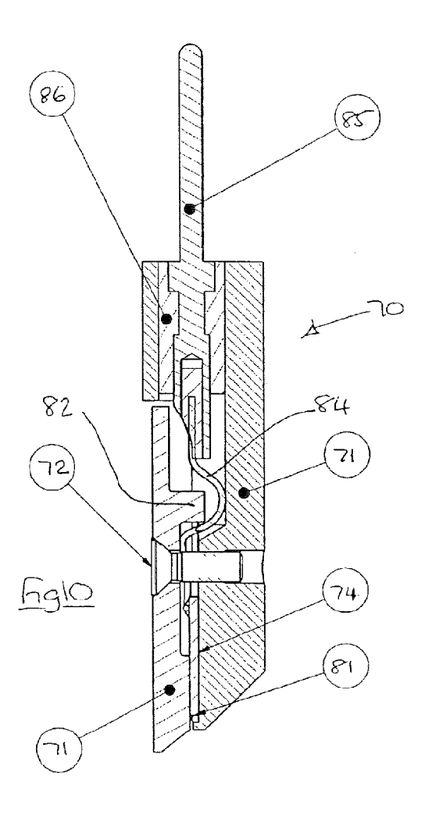
FIG. 10 is a transverse section of the tool of FIG. 9 on line '9'-'9'.

A tool body 71, of e.g. brass, has a piezo-electric crystal 74 mounted thereon. As illustrated the crystal is partially recessed, and the sidewalls thereof are electrically insulated by a filament 81 of e.g. nylon.

A tool 71 is mounted to the front face of the body 71 by a countersunk screw 72; the countersink ensures correct positioning of the tool, and rotation is avoided by means of a peg 82 guided in a slot 83 of the body 71.

One face (the rear side) of the crystal 74 makes electrical contact with the body 71, whereas the front face has a lead 84 soldered thereto and connected through the interior of the body to a protruding contact 85. A suitable potting material 86 insulates the contact pin 85 from the body 71.

The piezo-electric crystal is a commercially available product, having approximate dimensions of 4 mm×2 mm, and a thickness of 0.3 mm. The material of the crystal is typically a tough, hard non-conductive ceramic such as zirconia.

The anvil 71 has a downward projection 87 for contact with a test deposit.

In all embodiments the interface between the crystal and body, and between the anvil and crystal, may comprise a load distributing layer of e.g. epoxy resin. The resin is spread whilst fluid, and cures to provide a load path which is assuredly planar. Slight imperfections in manufacture or assembly are thereby avoided, and as a consequence point and line transfer of loads is obviated. When cured, an epoxy resin has the advantage of holding the components in a unitary assembly, In use the tool is mounted in a test head, is lowered against the substrate, and withdrawn by a specified distance, using known techniques. The tool is then driven against the deposit to be tested, and shearing loads are transmitted directly from the anvil 71 to the piezo crystal 74, where strain deformation causes an electrical signal representative of load to be passed to suitable recording and analysing equipment; which need not be further described here.

One problem with tools which sense forces using elements such as strain gauges and piezo-electric crystals, is to calibrate the tools. Often it is not possible to determine absolute values (such as breaking loads measured in grams), and the user must rely on relative values which allow comparison of results. This latter technique is acceptable where only one test tool is being used, but becomes problematic when the test tool requires to be substituted, or results from several similar tools must be compared.

Figure 11:
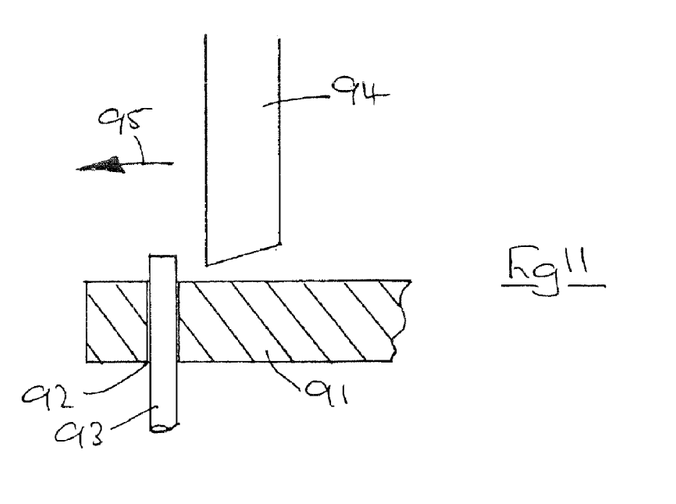
FIG. 11 illustrates a technique whereby the load/output of similar shear tools may be compared.

FIG. 11 illustrates a technique whereby the load/output of similar shear tools may be compared, and offers the possibility of also calibrating tools to give an absolute reading of breaking load.

A substrate 91 has an aperture 92 extending therethrough at right angles, and through which protrudes a wire 93. A test tool 94 driven in the direction of arrow 95 will shear the wire, and if suitably adapted can measure a relative breaking load. For example the tool may rely on electrical strain gauge or the piezo-electric crystal device described in this document.

The test may be repeated by indexing a further length of wire through the aperture. It will be appreciated that the length of wire above the aperture may not be critical, and that the test tool strikes the wire along the same axis at each test; these features make the test very simple to implement.

Wire is a very consistent material, and moreover is readily available as the precursor to the solder and gold balls which are applied to substrates used in semi-conductor devices. Accordingly calibration tests can be effected using the precise materials to be tested in commercial use of test tool.

The aperture 92 should preferably be close fitting to the wire 93 to ensure that the test tool strikes at right angles.

It has been established that a shear test according to this method gives results which have excellent repeatability. Any likely effect of variable wire protrusion can be easily checked by empirical tests, and if consistent equal wire feed is necessary, a suitable indexing device may be incorporated.

The technique thus permits similar tools, and nominally identical tools to be calibrated so that results from several different tools can be compared. The technique is of particular value in the case of calibration of production test tooling which may be used in many different manufacturing locations.

It will also be appreciated that, using known information concerning the strength and material of the wire, it is possible to obtain a much better indication of absolute breaking loads, so that the technique allows test tools to be calibrated to give a read-out in e.g. grams, newtons or any other suitable unit.

The invention claimed is:

1. A test apparatus for applying a shear load to a ball deposit on a substrate, the apparatus comprising:
   a support element; and
   a piezo-electric crystal on the support element,
   wherein the support element is adapted to apply the shear load to the ball deposit via said piezo-electric crystal, said piezo-electric crystal generating electrical signal in response to stress from the shear load.

2. The apparatus of claim 1 further comprising:
   a shield on said piezo-electric crystal, said shield configured to transfer the shear load from said piezo-electric crystal to the ball deposit.

3. The apparatus of claim 2 wherein said shield comprises a protective layer applied directly to said piezo-electric crystal.

4. The apparatus of claim 2 wherein said shield comprises a tool element mounted on said support element and adapted to bear against said piezo-electric crystal.

5. The apparatus of claim 4 wherein said tool element is arranged to pre-load said piezo-electric crystal in the intended direction of shear.

6. The apparatus of claim 2 wherein said shield includes a recess adapted to a shape of the ball deposit.

7. The apparatus of claim 6 wherein said recess is adapted to engage a spherical portion of the ball deposit.

8. The apparatus of claim 1 further comprising:
   a force distributing layer between said support element and said piezo-electric crystal.

9. The apparatus of claim 2 further comprising:
   a force distributing layer between said shield and said piezo-electric crystal.

10. The apparatus of claim 8 wherein said force distributing layer is adapted to give substantially uniform planar contact therebetween.

11. The apparatus of claim 8 wherein said force distributing layer comprises an electrical insulator or an electrically conductive material.

12. The apparatus of claim 8 wherein said force distributing layer comprises an electrically conductive material.

13. The apparatus of claim 10 wherein said support element includes an interface surface, said piezo-electric crystal includes an interface surface, and said force distributing layer comprises an epoxy resin adapted to be spread while fluid onto said interface surface of said support element and said interface surface of said piezo-electric crystal and cured after assembly to ensure planar contact therebetween.

14. The apparatus of claim 13 wherein said force distributing layer immovably bonds said interface surface of said support element and said interface surface of said piezo-electric crystal to define a unitary assembly.

15. A method of performing a shear test on a test tool, the method comprising:
   moving the test tool to contact a portion of a wire;
   shearing the portion of the wire by contact with the moving test tool;
   measuring a shear load applied to the moving test tool by the portion of the wire to perform the shear test; and
   comparing the measured shear load with a shear load measured by a different test tool moved to contact and shear another portion of the wire.

16. A method of performing a shear test on a test tool using a portion of a wire that projects through an aperture in a flat surface, the method comprising:
   indexing the portion of the wire through the aperture;
   moving the test tool to contact the portion of the wire;
   shearing the portion of the wire by contact with the moving test tool; and
   measuring a shear load applied to the moving test tool by the portion of the wire to perform the shear test.

17. The method of claim 16 further comprising:
   measuring a length of the portion of the wire relative to the flat surface.

18. A method of performing a shear test on a test tool, the method comprising:
   moving the test tool to contact a portion of a wire;
   shearing the portion of the wire by contact with the moving test tool;
   measuring a shear load applied to the moving test tool by the portion of the wire to perform the shear test; and
   moving the test tool to contact a ball deposit of gold or solder on a substrate of a type used in semiconductor devices.

19. A method of performing a shear test on a test tool using a wire comprised of gold or solder, the method comprising:
   providing a flat surface and an aperture extending through the flat surface that intersects the flat surface at a right angle;
   providing the wire in the aperture;
   indexing a portion of the wire to project above the flat surface;

after the portion of the wire is indexed to project above the flat surface, moving the test tool to contact the portion of the wire;

shearing the portion of the wire by contact with the moving test tool; and measuring a shear load applied to the moving test tool by the portion of the wire to perform the shear test.

20. A test apparatus for applying a shear load to a ball deposit on a substrate, the apparatus comprising:

a test head moveable relative to the substrate;

a test tool supported by the test head; and a piezo-electric crystal mounted on the test tool, wherein the test head is configured to move to contact the deposit with the test tool and apply a shear load to the deposit, thus placing the piezo-electric crystal under stress and causing an electrical signal to emanate from the piezo-electric crystal.

21. The test apparatus of claim 20 wherein the test tool is mounted vertically and has a top end and a bottom end, and the piezo-electric crystal is mounted closer to the bottom end of the test tool than to the top end of the test tool.

22. The test apparatus of claim 20 wherein the test tool has a larger end supported by the test head and a smaller end opposite to the larger end, and the piezo-electric crystal is mounted closer to the smaller end of the test tool than to the larger end of the test tool.

* * * * *

UNITED STATES PATENT AND TRADEMARK OFFICE
CERTIFICATE OF CORRECTION

PATENT NO. : 7,730,790 B2  Page 1 of 1
APPLICATION NO. : 11/573005
DATED : June 8, 2010
INVENTOR(S) : Robert John Sykes It is certified that error appears in the above-identified patent and that said Letters Patent is hereby corrected as shown below:

Column 5, line 51, Claim 1 after "generating", insert --an--

Signed and Sealed this

Twenty-eighth Day of September, 2010

David J. Kappos
*Director of the United States Patent and Trademark Office*